US012716069B2

(12) United States Patent
Tian et al.

(10) Patent No.: US 12,716,069 B2
(45) Date of Patent: Aug. 25, 2026

(54) **GENE COMBINATION FOR EXPRESSING AND PRODUCING TERREQUINONE A IN *ESCHERICHIA COLI* AND USE THEREOF**

(71) Applicant: Shanghai Academy of Agricultural Sciences, Shanghai (CN)

(72) Inventors: Yongsheng Tian, Shanghai (CN); Lijuan Wang, Shanghai (CN); Yongdong Deng, Shanghai (CN); Quanhong Yao, Shanghai (CN); Rihe Peng, Shanghai (CN); Jianjie Gao, Shanghai (CN); Zhenjun Li, Shanghai (CN); Wenhui Zhang, Shanghai (CN); Bo Wang, Shanghai (CN); Jing Xu, Shanghai (CN); Yu Wang, Shanghai (CN); Xiaoyan Fu, Shanghai (CN); Hongjuan Han, Shanghai (CN)

(73) Assignee: Shanghai Academy of Agricultural Sciences, Shanghai (CN)

( * ) Notice: Subject to any disclaimer, the term of this patent is extended or adjusted under 35 U.S.C. 154(b) by 603 days.

(21) Appl. No.: 18/322,932

(22) Filed: May 24, 2023

(65) Prior Publication Data

US 2024/0102025 A1 Mar. 28, 2024

(30) Foreign Application Priority Data

Sep. 20, 2022 (CN) ........................ 202211144379.4

(51) Int. Cl.
*C12N 15/70* (2006.01)
*C12P 17/16* (2006.01)

(52) U.S. Cl.
CPC ............ *C12N 15/70* (2013.01); *C12P 17/165* (2013.01)

(58) Field of Classification Search
CPC ................ C12N 15/70; C12N 2800/22; C12R 2001/19; C07K 14/38
See application file for complete search history.

*Primary Examiner* — Brian Gangle
*Assistant Examiner* — Lakia J Jackson-Tongue
(74) *Attorney, Agent, or Firm* — Patterson + Sheridan, LLP

(57) ABSTRACT

The present disclosure provides a gene combination for expressing and producing terrequinone A in *Escherichia coli* and use thereof. The gene combination includes a tdiAS gene, a tdiBS gene, a tdiCS gene, a tdiDS gene, a tdiES gene, an sfpS gene, an ScCKS gene, and an AtIPKS gene with nucleotide sequences set forth in SEQ ID NOS:1 to 8. In the present disclosure, a recombinant engineered strain capable of producing terrequinone A having anti-cancer activity is obtained by separately constructing recombinant plasmids pC02 and pU03 through the eight genes and transforming the two recombinant plasmids into *E. coli*. The content of terrequinone A in a fermentation broth thereof is 106.3 mg/L, which has potential application value in the biopharmaceutical field.

9 Claims, 3 Drawing Sheets

Specification includes a Sequence Listing.

GENE COMBINATION FOR EXPRESSING AND PRODUCING TERREQUINONE A IN *ESCHERICHIA COLI* AND USE THEREOF

CROSS REFERENCE TO RELATED APPLICATION

This patent application claims the benefit and priority of Chinese Patent Application No. 202211144379.4 filed with the China National Intellectual Property Administration on Sep. 20, 2022, the disclosure of which is incorporated by reference herein in its entirety as part of the present application.

REFERENCE TO SEQUENCE LISTING

A computer readable XML file entitled "HLP20230201303", that was created on Apr. 6, 2023, with a file size of about 56,389 bytes, contains the sequence listing for this application, has been filed with this application, and is hereby incorporated by reference in its entirety.

TECHNICAL FIELD

The present disclosure belongs to the field of gene engineering, in particular to a gene combination for expressing and producing terrequinone A in *Escherichia coli* and use thereof.

BACKGROUND

Bis-indolequinone compounds are a group of fungal natural products with bioactivities such as antiretroviral, antidiabetic or cytotoxic bioactivities. Since the discovery of cochliodinol, the family members of bis-indolequinone compounds are expanding. Herein, terrequinone A, which was first isolated from the desert plant rhizosphere fungus *Aspergillus terreus*, has moderate cytotoxicity against four human cancer cell lines (NCIH460, MCF-7, SF-268, and MIA Pa Ca-2) and is a potential anticancer drug (He et al., Journal of Natural Products, 2004, 67(12):1985-1991). Terrequinone A is also the only bis-indolequinone compound with biosynthetic information. In 2004, Bok et al. identified the biosynthetic gene cluster tdiABCDE responsible for the synthesis of terrequinone A by mining secondary metabolome from *Aspergillus nidulans* using the transcriptional regulator LaeA (Bok et al., Eukaryotic Cell, 2004, 3(2):527-535).

As a natural product, terrequinone A has a complex structure with plurality of functional groups. The chemical synthesis of terrequinone A requires many steps, resulting in low yield and environmental friendliness. With the elucidation of the special pathway for the biosynthesis and modification of terrequinone Ain vivo, biocatalytic synthesis of terrequinone A has become an effective attempt. Balibar et al. successfully synthesized terrequinone A by overexpressing and investigating five genes in gene cluster tdiABCDE and using an enzyme-catalyzed in vitro stepwise reaction (Carl J Balibar et al., Terrequinone A biosynthesis through L-tryptophan oxidation, dimerization and bisprenylation, Nature Chemical Biology, 2007, 3(9):584-592). However, synthesis in vitro requires the exogenous addition of expensive cofactors and cofactor regeneration enzyme systems; moreover, an enzyme-catalyzed product in the free enzymatic catalysis system tends to be the substrate of the next enzyme, and the delivery of substrates and products between enzymes is often limited by spatial constraints, reducing the efficiency of product synthesis. Therefore, a more efficient method is needed to produce terrequinone A. *E. coli*, as an excellent bioreactor, can be used for the biosynthesis of high-value natural products by modifying synthesis pathways thereof or introducing new metabolic pathways, which can perfectly avoid the above two problems.

SUMMARY

An objective of the present disclosure is to provide a gene combination for expressing and producing terrequinone A in *E. coli* and use thereof, thereby solving problems of high production cost and low synthesis efficiency in synthesis in vitro of terrequinone Ain the prior art.

To solve the above technical problems, the present disclosure provides the following technical solutions:

The first aspect of the present disclosure, where a gene combination for expressing and producing terrequinone A in *E. coli* is provided. The gene combination includes a tdiBS gene, a tdiCS gene, a tdiDS gene, a tdiES gene, an sfpS gene, an ScCKS gene, and an AtIPKS gene, where the tdiAS gene, the tdiBS gene, the tdiCS gene, the tdiDS gene, the tdiES gene, the sfpS gene, the ScCKS gene, and the AtIPKS gene have nucleotide sequences shown in SEQ ID NOS:1 to 8.

The second aspect of the present disclosure, where a recombinant plasmid pC02 for producing terrequinone A is provided. The recombinant plasmid pC02 is constructed by sequentially linking and ligating gene expression cassettes T7 tdiAS, T7 tdiBS, T7 tdiCS, T7 tdiDS, T7 tdiES, and T7 sfpS to an *E. coli* expression vector, where the gene expression cassettes T7 tdiAS, T7 tdiBS, T7 tdiCS, T7 tdiDS, T7 tdiES, and T7 sfpS are constructed by ligating each of a tdiAS gene, a tdiBS gene, a tdiCS gene, a tdiDS gene, a tdiES gene, and an sfpS gene with nucleotide sequences set forth in SEQ ID NOS:1 to 6 to a T7 promoter and a terminator.

In some embodiments, the *E. coli* expression vector is pCAMBIA1301.

The third aspect of the present disclosure, where a recombinant plasmid pU03 for producing dimethylallyl diphosphate (DMAPP) desired for terrequinone A synthesis is provided. The recombinant plasmid pU03 is constructed by sequentially linking and ligating gene expression cassettes T7 ScCKS and T7 AtIPKS to an *E. coli* expression vector, where the gene expression cassettes T7 ScCKS and T7 AtIPKS are constructed by ligating each of an ScCKS gene and an AtIPKS gene with nucleotide sequences set forth in SEQ ID NOS:7 to 8 to a T7 promoter and a terminator.

In some embodiments, the *E. coli* expression vector is pUC19.

The fourth aspect of the present disclosure, where a preparation method of a recombinant *E. coli* strain capable of producing terrequinone A, including the following steps: step S1: optimizing a tdiA gene, a tdiB gene, a tdiC gene, a tdiD gene, a tidE gene, an sfp gene, an ScCK gene, and an AtIPK gene according to an *E. coli* expression pattern to obtain a tdiAS gene, a tdiBS gene, a tdiCS gene, a tdiDS gene, a tdiES gene, an sfpS gene, an ScCKS gene, and an AtIPKS gene with nucleotide sequences set forth in SEQ ID NOS:1 to 8, where the eight genes ligate a T7 promoter and a terminator to construct gene expression cassettes T7 tdiAS, T7 tdiBS, T7 tdiCS, T7 tdiDS, T7 tdiES, T7 sfpS, T7 ScCKS, and T7 AtIPKS; step S2: ligating six gene expression cassettes conducted in step S1, the T7 tdiAS, the T7 tdiBS, the T7 tdiCS, the T7 tdiDS, the T7 tdiES, and the T7 sfpS, to an *E. coli* expression vector to obtain a recombinant plasmid pC02 containing gene expression cassettes tdiAS, tdiBS, tdiCS, tdiDS, tdiES, and sfpS; step S3: ligating two gene expression cassettes conducted in step S1, the T7 ScCKS and the T7 AtIPKS, to an *E. coli* expression vector to obtain a recombinant plasmid pU03 containing gene expression cassettes ScCKS and AtIPKS; and step S4: simultaneously transforming the recombinant plasmid pC02 obtained in step S2 and the recombinant plasmid pU03 obtained in step S3 into *E. coli* to obtain the recombinant *E. coli* strain capable of producing the terrequinone A.

In step S2, the six gene expression cassettes, namely, the T7 tdiAS, the T7 tdiBS, the T7 tdiCS, the T7 tdiDS, the T7 tdiES, and the T7 sfpS, are sequentially linked and ligated to an EcoRI endonuclease site at a 5'-end of the T7 tdiAS and a HindIII endonuclease site at a 3'-end of the T7 sfpS to obtain EcoRI-T7 tdiAS-T7 tdiBS-T7 tdiCS-T7 tdiDS-T7 tdiES-T7 sfpS-HindIII.

In step S3, the two gene expression cassettes, namely, the T7 ScCKS and the T7 AtIPKS, are sequentially linked and ligated to an EcoRI endonuclease site at a 5'-end of the T7 ScCKS and a HindIII endonuclease site at a 3'-end of the T7 AtIPKS to obtain EcoRI-T7 ScCKS-T7 AtIPKS-HindIII.

The fifth aspect of the present disclosure, a recombinant *E. coli* strain capable of producing terrequinone A obtained by the foregoing method is provided.

The sixth aspect of the present disclosure, where a method for producing terrequinone A using a recombinant *E. coli* strain is provided, namely, inoculating the recombinant *E. coli* strain in M9 liquid medium supplemented with 100 μg/mL ampicillin and 50 μg/mL kanamycin to culture at 37° C. until a bacterial suspension reaches an $OD_{600}$ of 0.6, adding 0.2% arabinose, continuing culturing at 25° C. for 14-18 h to obtain a fermentation broth, adding substrates L-tryptophan and prenol in the fermentation broth, and then culturing at 30° C. for 22-26 h to produce the terrequinone A. Each liter of the M9 liquid medium includes: 15 g of glycerol, 6 g of $Na_2HPO_4$, 3 g of $KH_2PO_4$, 1 g of $NH_4Cl$, 0.5 g of NaCl, 0.12 g of $MgSO_4$, 0.011 g of $CaCl_2$), 2.9 mg of $ZnSO_4 \cdot 7H_2O$, 0.2 mL of 1% (w/v) vitamin B1, and 5 g of acid-hydrolyzed casein.

An embodiment of the present disclosure, where recombinant *E. coli* BL-3 is inoculated in optimized M9 liquid medium supplemented with 100 μg/mL ampicillin and 50 μg/mL kanamycin (15 g of glycerol, 6 g of $Na_2HPO_4$, 3 g of $KH_2PO_4$, 1 g of $NH_4Cl$, 0.5 g of NaCl, 0.12 g of $MgSO_4$, 0.011 g of $CaCl_2$), 2.9 mg of $ZnSO_4 \cdot 7H_2O$, 0.2 mL of 1% (w/v) vitamin B1, and 5 g of acid-hydrolyzed casein per liter), cultured at 37° C. until the bacterial suspension reaches an $OD_{600}$ of 0.6, added with 0.2% arabinose, and kept culturing at 25° C. for 16 h to obtain a fermentation broth; the substrates L-tryptophan and prenol are added to the fermentation broth and cultured at 30° C. for 24 to produce the terrequinone A.

In some embodiments, 0.75 g/L L-tryptophan and 0.95 g/L prenol may be added to the fermentation broth.

In the present disclosure, the tdiA gene, the tdiB gene, the tdiC gene, the tdiD gene, the tidE gene, the sfp gene, the ScCK gene, and the AtIPK gene are optimized as a whole based on the codon preference of *E. coli*. The optimization principles include: (I) optimizing genes and gene codons to improve the translation efficiency of the genes based on the codon preference of *E. coli*; (II) eliminating stem-loop structures, transcription termination signals, and reverse repeats within 200 bp of the same or adjacent genes, and balancing the GC/AT content within the genes to improve RNA stability; (III) ensuring that gene encoding proteins comply with the N-end rule to improve the stability of translated proteins; (IV) optimizing the free energy of mRNA secondary structure to improve gene expression efficiency; and (V) on the basis of meeting the above four principles, selecting and eliminating EcoRI and HindIII restriction endonuclease recognition sites within the four genes to facilitate the construction of recombinant plasmids. The tdiAS gene, the tdiBS gene, the tdiCS gene, the tdiDS gene, the tdiES gene, the sfpS gene, the ScCKS gene, and the AtIPKS gene are obtained after optimization.

The present disclosure chemically synthesizes a tdiAS gene encoding nonribosomal peptide synthetase (NRPS), a tdiBS gene encoding indole prenyltransferase, a tdiCS gene encoding oxidoreductase, a tdiDS gene encoding aminotransferase, a tdiES gene encoding chaperone, an sfpS gene encoding phosphopantetheinyl transferase, an ScCKS gene encoding choline kinase, and an AtIPKS gene encoding isopentenyl phosphate kinase. For the first time, the eight gene fragments each are ligated to the T7 promoter and terminator of *E. coli* to construct the corresponding gene expression cassettes. Six gene expression cassettes, T7 tdiAS, T7 tdiBS, T7 tdiCS, T7 tdiDS, T7 tdiES, and T7 sfpS, are ligated to an *E. coli* expression vector to obtain a recombinant plasmid pC02. Two gene expression cassettes, T7 ScCKS and T7 AtIPKS, are ligated to an *E. coli* expression vector to obtain a recombinant plasmid pU03. Both the pC02 and the pU03 are transformed into *E. coli* to obtain a recombinant engineered strain capable of producing terrequinone A, which has an anti-cancer activity. The content of terrequinone A in a fermentation broth thereof can reach 106.3 mg/L when 0.75 g/L L-tryptophan and 0.95 g/L prenol are added.

Compared with the prior art, the present disclosure has the following beneficial effects:

Using synthetic biology technology, the present disclosure optimizes the tdiA gene, the tdiB gene, the tdiC gene, the tdiD gene, the tidE gene, the sfp gene, the ScCK gene, and the AtIPK gene according to an *E. coli* expression pattern. After optimization, these genes are separately ligated to the T7 promoter and terminator of *E. coli* to construct gene expression cassettes. The gene expression cassettes are ligated to the *E. coli* expression vector to obtain a polygenic *E. coli* transformation vector to construct a genetically engineered strain, which can express active genes of the tdiAS gene encoding NRPS, the tdiBS gene encoding methylpropanoyl-L-tryptophan synthetase, the tdiCS gene encoding oxidoreductase, the tdiDS gene encoding aminotransferase, the tdiES gene encoding chaperone, the sfpS gene encoding phosphopantetheinyl transferase, the ScCKS gene encoding choline kinase, and the AtIPKS gene encoding isopentenyl phosphate kinase. The genetically engineered strain can also use L-tryptophan and prenol as substrates to produce terrequinone A with anti-cancer activity. which has potential application value in the biopharmaceutical field.

In the terrequinone A synthesis pathway of *A. nidulans*, synthesis of each terrequione A molecule requires consumption of two DMAPP molecules. The DMAPP produced by original MEP pathway of *E. coli* cannot meet the demand for terrequione A synthesis. In the present disclosure, a multi-gene transformation vector pU03 are simultaneously transformed into *E. coli* to obtain a recombinant strain, which can provide sufficient DMAPP for terrequinone A synthesis using prenol as substrate.

He et al. isolated 6.0 mg of terrequinone A powder from 5.4 L of fermentation broth 28 days after culture of *A. terreus* (He et al., Journal of Natural Products, 2004, 67(12):1985-1991). Compared with natural strain *A. terreus*, at 48 h after the culture of the recombinant *E. coli* strain in the present disclosure, the content of terrequinone A in the fermentation broth can reach 106.3 mg/L, with significant improvement in both transformation rate and product concentration.

DETAILED DESCRIPTION OF THE EMBODIMENTS

Figure 1:
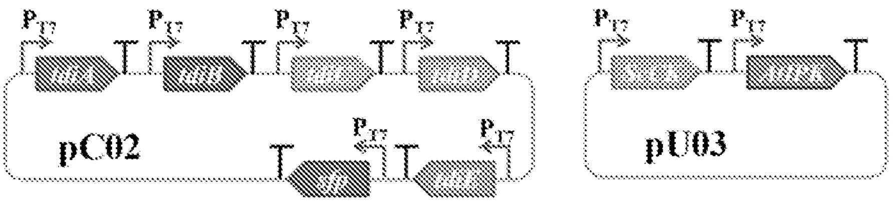
FIG. 1 schematically illustrates the structure of recombinant plasmids pC02 and pU03 in Example 3 of the present disclosure.

The present disclosure will be further described below with reference to the drawings and specific Examples.

The test methods used in the Examples are conventional molecular biology methods, unless otherwise specified. The materials and reagents used are commercially available, unless otherwise specified.

Example 1 Optimization of Eight Gene Fragments

Based on coding sequences of tdiA (Genbank: EF550581.1), tdiB (Genbank: EF550582.1), tdiC (Genbank: EF550583.1), tdiD (Genbank: EF550584.1), tidE (Genbank: EF550585.1), sfp (GenBank: X65610.1, *Bacillus subtilis*), ScCK (GenBank: AAA34499.1, *Saccharomyces cerevisiae*), and AtIPK (GenBank: AY150412.1, *Arabidopsis thaliana*) genes, the above eight genes were optimized as a whole according to the following principles:

(I) genes and gene codons were optimized to improve the translation efficiency of the genes based on the codon preference of *E. coli*; (II) stem-loop structures, transcription termination signals, and reverse repeats within 200 bp of the same or adjacent genes were eliminated and the GC/AT content within the genes are balanced to improve RNA stability; (III) gene encoding proteins was ensured to comply with the N-end rule to improve the stability of translated proteins; (IV) the free energy of mRNA secondary structure was optimized to improve gene expression efficiency; and (V) on the basis of meeting the above four principles, EcoRI and HindIII restriction endonuclease recognition sites within the eight genes were selected and eliminated to facilitate the construction of recombinant plasmids.

The tdiAS gene, the tdiBS gene, the tdiCS gene, the tdiDS gene, the tdiES gene, the sfpS gene, the ScCKS gene, and the AtIPKS gene were obtained after optimization. The tdiAS gene has the nucleotide sequence set forth in SEQ ID NO:1; the tdiBS gene has the nucleotide sequence set forth in SEQ ID NO:2; the tdiCS gene has the nucleotide sequence set forth in SEQ ID NO:3; the tdiDS gene has the nucleotide sequence set forth in SEQ ID NO:4; the tdiES gene has the nucleotide sequence set forth in SEQ ID NO:5; the sfpS gene has the nucleotide sequence set forth in SEQ ID NO:6; the ScCKS gene has the nucleotide sequence set forth in SEQ ID NO:7; and the AtIPKS gene has the nucleotide sequence set forth in SEQ ID NO:8.

Example 2 Construction of Gene Expression Cassettes

T7 promoter sequence of *E. coli* was ligated at the front end of each optimized gene sequence and T7 terminator sequence of *E. coli* was ligated at the end of each optimized gene to construct gene expression cassettes T7 tdiAS, T7 tdiBS, T7 tdiCS, T7 tdiDS, T7 tdiES, T7 sfpS, T7 ScCKS, and T7 AtIPKS, which were chemically synthesized by Nanjing GenScript Biotech Corporation.

```
The T7 promoter sequence
(SEQ ID NO: 9) was:
5'-TAATACGACTCACTATAGG-3';

The T7 terminator sequence
(SEQ ID NO: 10) was:
5'-TAGCATAACCCCTTGGGGCCTCTA

AACGGGTCTTGAGGGGTTTTTTG-3'.
```

Example 3 Construction and Transformation of Recombinant Plasmids

The "polyacrylamide gel electrophoresis (PAGE)-mediated gene splicing by overlap extension PCR" technology (Peng R H et al., A direct and efficient PAGE-mediated overlap extension PCR method for gene multiple-site mutagenesis, Appl Microbiol Biotechnol. 2006, 73(1):234-40) was used to sequentially link and ligate the six constructed gene expression cassettes, T7 tdiAS, T7 tdiBS, T7 tdiCS, T7 tdiDS, T7 tdiES, and T7 sfpS, to the EcoRI endonuclease recognition site at the 5'-end of the T7 tdiAS and the HindIII endonuclease recognition site at the 3'-end of the T7 sfpS to obtain EcoRI-T7 tdiAS-T7 tdiBS-T7 tdiCS-T7 tdiDS-T7 tdiES-T7 sfpS-HindIII, and to sequentially link and ligate the two gene expression cassettes, T7 ScCKS and T7 AtIPKS, to the EcoRI endonuclease recognition site at the 5'-end of the T7 ScCKS and the HindIII endonuclease recognition site at the 3'-end of the T7 AtIPKS to obtain EcoRI-T7 ScCKS-T7 AtIPKS-HindIII.

In order to obtain EcoRI-T7 tdiAS-T7 tdiBS-T7 tdiCS-T7 tdiDS-T7 tdiES-T7 sfpS-HindIII, the designed primer sequences (SEQ ID NOS:11 to 22) were as follows:

```
T7 tdiAS:
P1:
                              (SEQ ID NO: 11)
5'-GAATCCTAATACGACTCACTATA

GGATGGCACCATCTAAG-3';

P2:
                              (SEQ ID NO: 12)
5'-GTATTCAGTAGCCATCCTATAGTGAGTC

GTATTACAAAAAACCCCTC-3';
```

-continued

```
T7 tdiBS:
P3:
                                          (SEQ ID NO: 13)
5'-TTGAGGGGTTTTTTGTAATACGACTCAC

TATAGGATGGCTACTGAATAC-3';

P4:
                                          (SEQ ID NO: 14)
5'-AAGAGCTGCGTGCATCCTATAGTGAGTC

GTATTACAAAAAACCCCTC-3';

T7 tdiCS:
P5:
                                          (SEQ ID NO: 15)
5'-TTGAGGGGTTTTTTGTAATACGACTCAC

TATAGGATGCACGCAGCTCTT-3';

P6:
                                          (SEQ ID NO: 16)
5'-ACCAATAGAACCCATCCTATAGTGAGTC

GTATTACAAAAAACCCCTC-3';

T7 tdiDS:
P7:
                                          (SEQ ID NO: 17)
5'-TTGAGGGGTTTTTTGTAATACGACTCAC

TATAGGATGGGTTCTATTGGT-3';

P8:
                                          (SEQ ID NO: 18)
5'-ATGGTCTGTTAACCATCCTATAGTGAGT

CGTATTACAAAAAACCCCTC-3';

T7 tdiES:
P9:
                                          (SEQ ID NO: 19)
5'-TTGAGGGGTTTTTTGTAATACGACTCAC

TATAGGATGGTTAACAGACCAT-3';

P10:
                                           (SEQ ID NO:20)
5'-ACCGTAGATTTTCATCCTATAGTGAGTC

GTATTACAAAAAACCCCTC-3';

T7 spfS:
P11:
                                          (SEQ ID NO: 21)
5'-TTGAGGGGTTTTTTGTAATACGACTCAC

TATAGGATGAAAATCTACGGT-3';
and

P12:
                                          (SEQ ID NO: 22)
5'-AAGCTTCAAAAAACCCCTCAAGACCCGT

TTAGAGG-3'.
```

First-step PCR: PCR amplification was conducted using gene fragments of T7 tdiAS, T7 tdiBS, T7 tdiCS, T7 tdiDS, T7 tdiES, and T7 sfpS as templates separately, and adding the corresponding primers to obtain six gene fragments. The PCR amplification program was as follows: 94° C. for 30 s, 68° C. for 60 s, for a total of 10 cycles.

The six gene fragments obtained in the first-step PCR were subjected to gel electrophoresis and gel extraction.

Second-step PCR: PCR amplification was conducted using a mixture of the six gene fragments obtained by gel extraction as a template and P1 and P12 as primers. The PCR amplification program was as follows: initial denaturation at 94° C. for 1 min; 25 cycles of denaturation at 94° C. for 30 s, annealing at 58° C. for 30 s, and extension at 72° C. for 30 s; and finally extension at 72° C. for 10 min. In order to obtain EcoRI-T7 tdiAS-T7 tdiBS-T7 tdiCS-T7 tdiDS-T7 tdiES-T7 sfpS-HindIII, the designed primer sequences (SEQ ID NOS:23 to 26) were as follows:

```
T7 ScCKS:
P13:
                                          (SEQ ID NO: 23)
5'-GAATCCTAATACGACTCACTATAGGAT

GGTTCAAGAGT-3';

P14:
                                          (SEQ ID NO: 24)
5'-CTTCTCCAGCTCGTTCCCTATAGTGAG

TCGTATTACAAAAAACCCCTC-3';

T7 AtIPKS:
P15:
                                          (SEQ ID NO: 25)
5'-TTGAGGGGTTTTTTGTAATACGACTCA

CTATAGGGAACGAGCTGGAGAAG-3';
and

P16:
                                          (SEQ ID NO: 26)
5'-AAGCTTCAAAAAACCCCTCAAGACCCG

TTTAGAGG-3'.
```

First-step PCR: PCR amplification was conducted using gene fragments of T7 ScCKS and T7 AtIPKS as templates separately, and adding the corresponding primers to obtain two gene fragments. The PCR amplification program was as follows: 94° C. for 30 s, 68° C. for 60 s, for a total of 10 cycles.

The two gene fragments obtained in the first-step PCR were subjected to gel electrophoresis and gel extraction.

Second-step PCR: PCR amplification was conducted using a mixture of the two gene fragments obtained by gel extraction as a template and P13 and P16 as primers. The PCR amplification program was as follows: initial denaturation at 94° C. for 1 min; 25 cycles of denaturation at 94° C. for 30 s, annealing at 58° C. for 30 s, and extension at 72° C. for 30 s; and finally extension at 72° C. for 10 min. The above tandem six-gene fragment EcoRI-T7 tdiAS-T7 tdiBS-T7 tdiCS-T7 tdiDS-T7 tdiES-T7 sfpS-HindIII was double digested with EcoRI and HindIII and ligated to a vector, pCAMBIA1301, obtained by the same digestion to obtain a recombinant plasmid pC02 containing six genes; the two-gene fragment EcoRI-T7 ScCKS-T7 AtIPKS-HindIII was double digested with EcoRI and HindIII and ligated to a vector, pUC19, obtained by the same digestion to obtain a recombinant plasmid pU03 containing two genes (as shown in FIG. 1).

Figure 2:
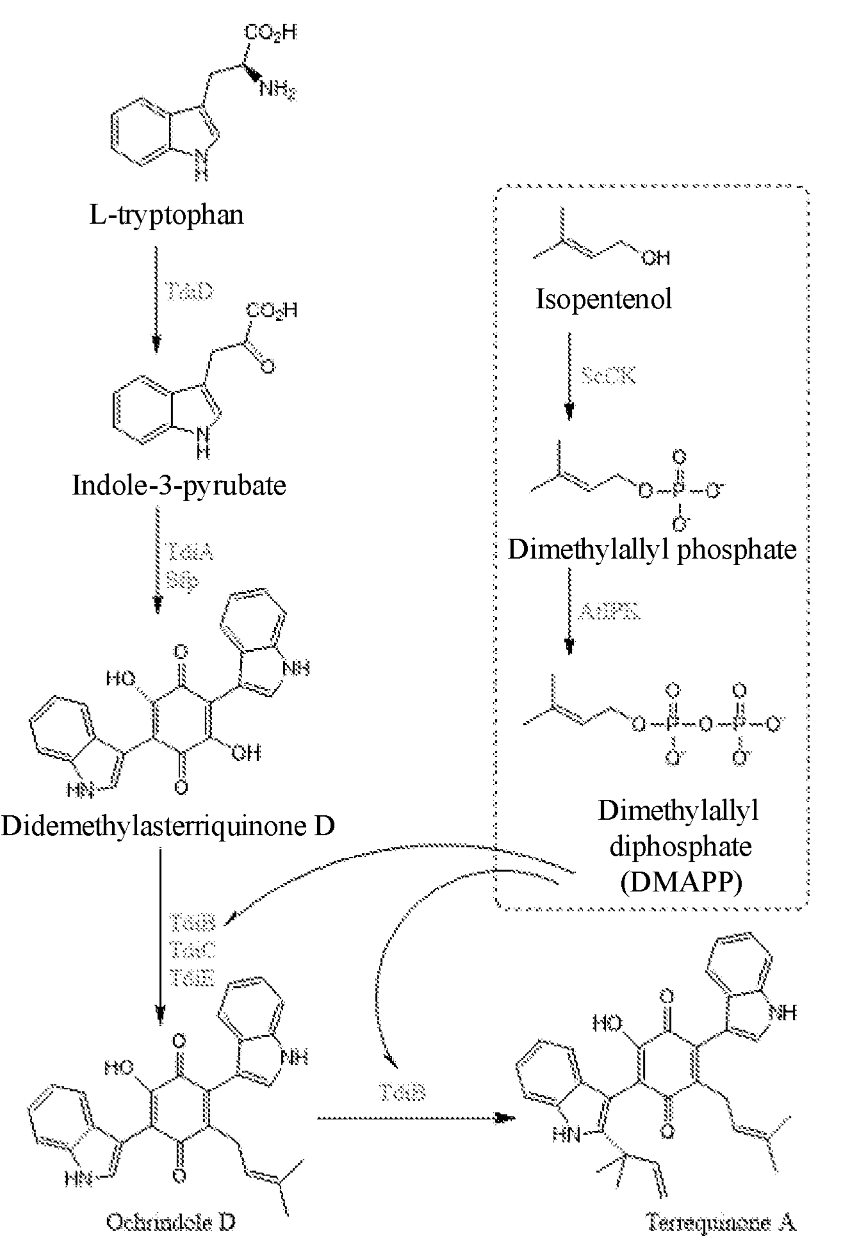
FIG. 2 illustrates a synthesis pathway of terrequinone A by *E. coli* BL-3 transformation in Example 3 of the present disclosure.

Both pC02 and pU03 were simultaneously transformed into *E. coli* BL21-AI by the heat shock method, spread on an LB solid plate supplemented with 100 μg/mL ampicillin and 50 g/mL kanamycin, and cultured at 37° C. overnight to pick the positive clone, namely recombinant *E. coli* BL-3. The synthesis pathway of terrequinone A by its transformation is shown in FIG. 2.

Example 4 Identification of Recombinant *E. coli* Strain

Successful transformation of exogenous genes into *E. coli* was identified by PCR. A single colony was picked and inoculated in LB liquid supplemented with 100 μg/mL ampicillin and 50 μg/mL kanamycin, cultured at 37° C. until the bacterial suspension reached an $OD_{600}$ of 0.6, and centrifuged at 10,000 rpm for 1 min at 4° C. to collect cells. Plasmid DNA was extracted from the cells by the Trizol method; using extracted plasmid as a PCR template, exogenous tdiAS, tdiBS, tdiCS, tdiDS, tdiES, sfpS, ScCKS, and AtIPKS genes were detected by PCR using the following primers and amplification conditions.

Sequences of primers used for PCR (SEQ ID NOS:27 to 42) were as follows, where the primer were designed based on specific fragments of each gene:

```
tdiA-F:
                              (SEQ ID NO: 27)
5'-TCCGTCAAGTGCATGGATGTC-3';

tdiA-R:
                              (SEQ ID NO: 28)
5'-CAGACCACGCTCACGCAGGAC-3';

tdiB-F:
                              (SEQ ID NO: 29)
5'-GCACTGAAGAAGCTGGGTAAC-3';

tdiB-R:
                              (SEQ ID NO: 30)
5'-ACGGAAACCGAAGTCACCAGC-3';

tdiC-F:
                              (SEQ ID NO: 31)
5'-ATCTCTCGTAAGCCAATCTGC-3';

tdiC-R:
                              (SEQ ID NO: 32)
5'-GACGATGACGACACGGGAACC-3';

tdiD-F:
                              (SEQ ID NO: 33)
5'-ATGTTCGTCTGGCTGGAACTC-3';

tdiD-R:
                              (SEQ ID NO: 34)
5'-GCAACGATCGACCAGACCAGC-3';

tdiE-F:
                              (SEQ ID NO: 35)
5'-AAGACCTTGGGTTTGTGGAAC-3';

tdiE-R:
                              (SEQ ID NO: 36)
5'-GACGTCGGAACCAGGTGCAGC-3';

sfp-F:
                              (SEQ ID NO: 37)
5'-TCTCACTCTGGACGTTGGGTG-3';

sfp-R:
                              (SEQ ID NO: 38)
5'-TGCAGATGCGATGAGACGTTG-3';

ScCK-F:
                              (SEQ ID NO: 39)
5'-GGTCCTAACGGCAAGAAGTAC-3';

ScCK-R:
                              (SEQ ID NO: 40)
5'-GGAGGAGAAGTTCTTGCACTC-3';

AtIPK-F:
                             (SEQ ID NO: 41)
5'-CCACTGTTGGAGCACACTGAC-3';
and

AtIPK-R:
                              (SEQ ID NO: 42)
5'-GGAGAAACGGATGATAGTACC-3'.
```

The amplification program used was as follows: initial denaturation at 94° C. for 3 min; 30 cycles of denaturation at 94° C. for 30 s, annealing at 54° C. for 30 s, and extension at 72° C. for 30 s; and finally extension at 72° C. for 10 min. The results are shown in FIG. 2.

Figure 3:
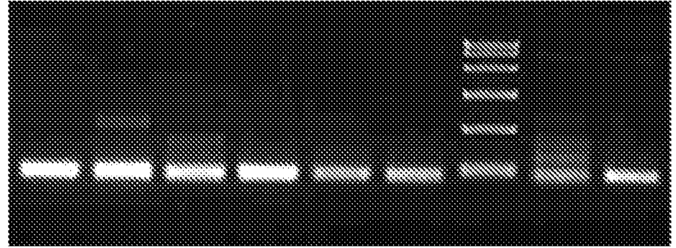
FIG. 3 illustrates a PCR result of exogenous genes of *E. coli* BL-3 in Example 4 of the present disclosure, where M represents Marker.

The results in FIG. 3 showed that the recombinant *E. coli* BL-3 provided by the present disclosure could amplify the above eight genes, tdiAS, tdiBS, tdiCS, tdiDS, tdiES, sfpS, ScCKS, and AtIPKS, indicating that both recombinant plasmids, pC02 and pU03, were transformed into *E. coli* and the obtained recombinant *E. coli* BL-3 included the eight exogenous genes.

Example 5 Production of Terrequinone a by Recombinant *E. coli* BL-3

A single colony transformed with polygenic recombinant plasmids pC02 and pU03 in Example 3 of the present disclosure was picked and inoculated in optimized M9 liquid medium supplemented with 100 μg/mL ampicillin and 50 μg/mL kanamycin (15 g of glycerol, 6 g of $Na_2HPO_4$, 3 g of $KH_2PO_4$, 1 g of $NH_4Cl$, 0.5 g of NaCl, 0.12 g of $MgSO_4$, 0.011 g of $CaCl_2$), 2.9 mg of $ZnSO_4 \cdot 7H_2O$, 0.2 mL of 1% (w/v) vitamin B1, and 5 g of acid-hydrolyzed casein per liter). The single colony was cultured at 37° C. until the bacterial suspension reached an $OD_{600}$ of 0.6. 0.2% L-arabinose (final concentration) was added, and the culture was continued at 25° C. for 16 h to obtain a fermentation broth. 0.5 g/L L-tryptophan and equal amount of substance of prenol were added to the fermentation broth and cultured at 30° C. for 24 h.

200 μL of fermentation broth was added with twice the volume of methanol to broken cells by ultrasound (ultrasound is conducted at a power of 400 W for 4 s, at an interval of 8 s, repeated for 99 rounds). After centrifugation at 10,000 rpm for 1 min at 4° C., the supernatant was collected, extracted with an equal volume of chloroform, evaporated under reduced pressure, and reconstituted in methanol for terrequinone A detection.

Figure 4:
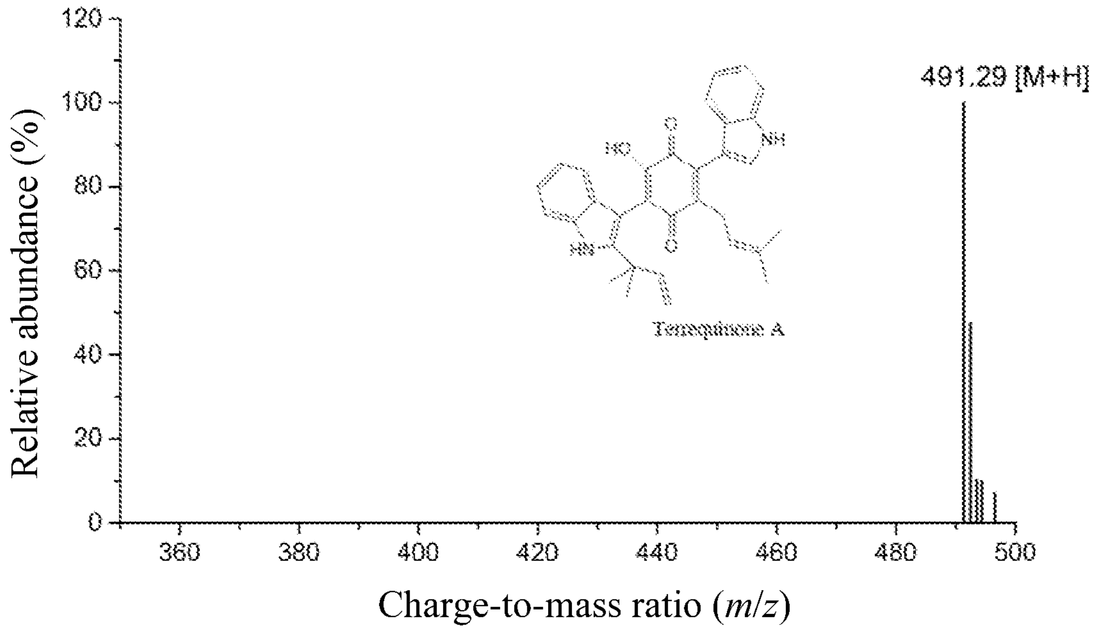
FIG. 4 illustrates the mass spectrometry (MS) identification of terrequinone A in Example 5 of the present disclosure (positive ion m/z=491.2)

Through liquid chromatography mass spectrometry (LC-MS), the mass spectrum of the sample (as shown in FIG. 4) was compared with the reported mass spectrum of terrequinone A in literature (Balibar et al., Nature Chemical Biology, 2007, 3(9):584-592), and the sample was identified as terrequinone A. The specific LC-MS conditions were as follows: TSQ Quantum-Accela LC-MS System; Shimadzu Shim-pack GIST C18 column (150×2.1 mm, 3 m); mobile phase A of 0.1% formic acid in water, and mobile phase B of 0.1% formic acid in acetonitrile were used. The LC-MS is conducted by gradient elution: 0-3 min: 20% B; 3-13 min: 20% B to 90% B; with a flow rate of 0.2 μL/min, a column temperature of 35° C., a sampling volume of 1 μL, an ion source in ESI+ mode, an electrospray voltage of 3,500 V, an sheath gas flow rate of 13 mL/min, an ion transfer tube temperature of 275° C., a scan mode of full scan mode, a scan resolution of 0.4 Da, an acquired mass-to-charge ratio range of m/z=300-500 Da, a scan time of 0.5 s.

Figure 5:
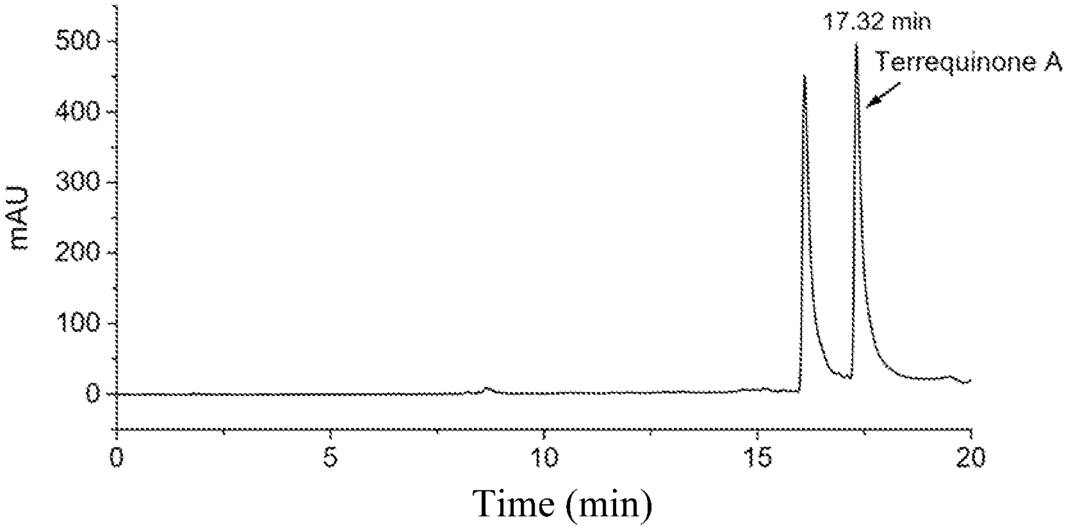
FIG. 5 illustrates high performance liquid chromatography (HPLC) of a chloroform-extracted bacterial culture medium in Example 5 of the present disclosure.

The content of terrequinone A was determined by HPLC. Specific HPLC detection conditions were as follows: Agilent 1100 High Performance Liquid Chromatography System, C18 column (120 Å, 4.6×150 mm, 5 μm), mobile phase of 0.1% trifluoroacetic acid-acetonitrile-water were used. And the HPLC is conducted by gradient elution from 5% to 100% in 20 min with a flow rate of 1 mL/min, a column temperature of 35° C., a detection wavelength of 280 nm and an sampling volume of 20 μL. The determined content of terrequinone A was 41.9 mg/L (FIG. 5).

Example 6 Effect of Substrate Addition on Production of Terrequinone a by Recombinant *E. coli* BL-3

Figure 6:
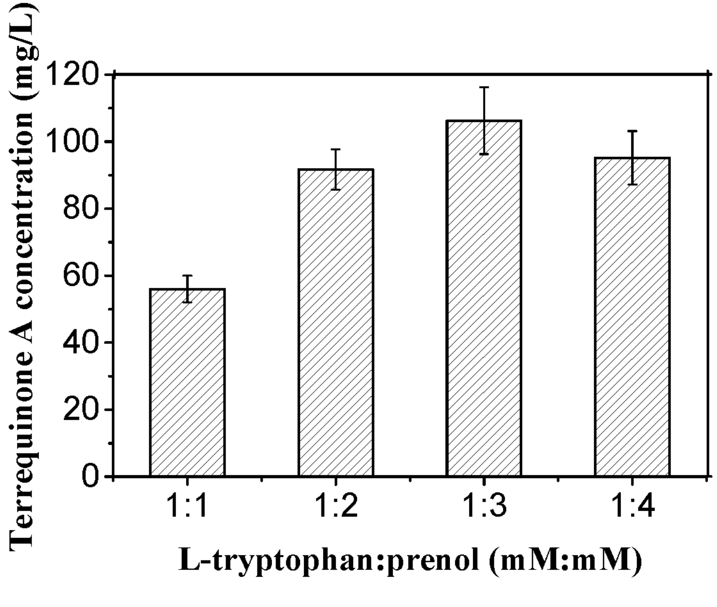
FIG. 6 illustrates the content of terrequinone A after addition of substrates in different concentrations in Example 6 of the present disclosure.

A single colony of recombinant *E. coli* BL-3 obtained in Example 3 was picked, inoculated in 50 mL of optimized M9 liquid medium supplemented with 100 μg/mL ampicillin and 50 μg/mL kanamycin. The single colony was cultured at 37° C. until the bacterial suspension reached an $OD_{600}$ of 0.6. 0.2% arabinose was added, and the culture was continued at 25° C. for 16 h to obtain a fermentation broth. 0.75 g/L L-tryptophan and prenol of different concentrations (0.32, 0.63, 0.95, and 1.27 g/L) were added to the fermentation broth to make the molar ratio of L-tryptophan and prenol reach 1:1, 1:2, 1:3, and 1:4, and cultured at 30° C. for 24 h. The content of terrequinone A in BL-3 fermentation broth was determined under different substrate addition. As shown in FIG. 6, when the molar ratio of L-tryptophan and prenol was 1:3 (0.75 g/L L-tryptophan and 0.95 g/L prenol), the terrequinone A in the fermentation broth of the recombinant *E. coli* strain herein could reach 106.3 mg/L; however, the terrequinone A powder could be separated from 5.4 L of fermentation broth after culturing natural strain *A. terreus* for 28 days was 6.0 mg. According to the results, the recombinant *E. coli* BL-3 provided by the present disclosure shows significant improvement in both transformation rate and terrequinone A product concentration.

The above are only the preferred examples of the present disclosure and are not intended to limit the scope of the present disclosure. Various changes can also be made to the above examples of the present disclosure. All simple and equivalent changes and modifications made in accordance with the claims and specification of the present disclosure fall within the claimed scope of the present disclosure. All that is not described in detail in the present disclosure is conventional technical content.

What is claimed is:

1. A recombinant plasmid composition for producing terrequinone A, comprising recombinant plasmid pC02 and recombinant plasmid pU03, wherein the recombinant plasmid pC02 is constructed by sequentially linking and ligating gene expression cassettes T7 tdiAS, T7 tdiBS, T7 tdiCS, T7 tdiDS, T7 tdiES, and T7 sfpS to an *Escherichia coli* expression vector, wherein the gene expression cassettes T7 tdiAS, T7 tdiBS, T7 tdiCS, T7 tdiDS, T7 tdiES, and T7 sfpS are constructed by ligating each of a tdiAS gene, a tdiBS gene, a tdiCS gene, a tdiDS gene, a tdiES gene, and an sfpS gene with nucleotide sequences set forth in SEQ ID NOS: 1 to 6 to a T7 promoter and a terminator; wherein the recombinant plasmid pU03 for producing dimethylallyl diphosphate (DMAPP) desired for terrequinone A synthesis, wherein the recombinant plasmid pU03 is constructed by sequentially linking and ligating gene expression cassettes T7 ScCKS and T7 AtIPKS to an *Escherichia coli* expression vector, wherein the gene expression cassettes T7 ScCKS and T7 AtIPKS are constructed by ligating each of an ScCKS gene and an AtIPKS gene with nucleotide sequences set forth in SEQ ID NOS: 7 to 8 to a T7 promoter and a terminator.

2. The recombinant plasmid pC02 according to claim 1, wherein the *Escherichia coli* expression vector is pCAMBIA1301.

3. The recombinant plasmid pU03 according to claim 1, wherein the *Escherichia coli* expression vector is pUC19.

4. A preparation method of a recombinant *Escherichia coli* strain capable of producing terrequinone A, comprising the following steps:

step S1: optimizing a tdiA gene, a tdiB gene, a tdiC gene, a tdiD gene, a tidE gene, an sfp gene, an ScCK gene, and an AtIPK gene according to an *Escherichia coli* expression pattern to obtain eight genes, namely, a tdiAS gene, a tdiBS gene, a tdiCS gene, a tdiDS gene, a tdiES gene, an sfpS gene, an ScCKS gene, and an AtIPKS gene with nucleotide sequences set forth in SEQ ID NOS: 1 to 8, ligating each of the eight genes to a T7 promoter and a terminator to construct gene expression cassettes T7 tdiAS, T7 tdiBS, T7 tdiCS, T7 tdiDS, T7 tdiES, T7 sfpS, T7 ScCKS, and T7 AtIPKS;

step S2: sequentially linking and ligating six gene expression cassettes obtained in step S1, namely, the T7 tdiAS, the T7 tdiBS, the T7 tdiCS, the T7 tdiDS, the T7 tdiES, and the T7 sfpS, to an *Escherichia coli* expression vector to obtain a recombinant plasmid pC02 comprising six gene expression cassettes tdiAS, tdiBS, tdiCS, tdiDS, tdiES, and sfpS;

step S3: sequentially linking and ligating two gene expression cassettes obtained in step S1, namely, the T7 ScCKS and the T7 AtIPKS, to an *Escherichia coli* expression vector to obtain a recombinant plasmid pU03 comprising two gene expression cassettes ScCKS and AtIPKS; and step S4: simultaneously transforming the recombinant plasmid pC02 obtained in step S2 and the recombinant plasmid pU03 obtained in step S3 into *Escherichia coli* to obtain the recombinant *Escherichia coli* strain capable of producing the terrequinone A.

5. The preparation method of a recombinant *Escherichia coli* strain capable of producing terrequinone A according to claim 4, wherein in the step S2, the six gene expression cassettes, namely, the T7 tdiAS, the T7 tdiBS, the T7 tdiCS, the T7 tdiDS, the T7 tdiES, and the T7 sfpS, are sequentially linked and ligated to an EcoRI endonuclease site at a 5'-end of the T7 tdiAS and a HindIII endonuclease site at a 3'-end of the T7 sfpS to obtain EcoRI-T7 tdiAS-T7 tdiBS-T7 tdiCS-T7 tdiDS-T7 tdiES-T7 sfpS-HindIII.

6. The preparation method of a recombinant *Escherichia coli* strain capable of producing terrequinone A according to claim 4, wherein in the step S3, the two gene expression cassettes, namely, the T7 ScCKS and the T7 AtIPKS, are sequentially linked and ligated to an EcoRI endonuclease site at a 5'-end of the T7 ScCKS and a HindIII endonuclease site at a 3'-end of the T7 AtIPKS to obtain EcoRI-T7 ScCKS-T7 AtIPKS-HindIII.

7. A recombinant *Escherichia coli* strain capable of producing terrequinone A obtained by the following steps:

step S1: optimizing a tdiA gene, a tdiB gene, a tdiC gene, a tdiD gene, a tidE gene, an sfp gene, an ScCK gene, and an AtIPK gene according to an *Escherichia coli* expression pattern to obtain eight genes, namely, a tdiAS gene, a tdiBS gene, a tdiCS gene, a tdiDS gene, a tdiES gene, an sfpS gene, an ScCKS gene, and an AtIPKS gene with nucleotide sequences set forth in SEQ ID NOS: 1 to 8, ligating each of the eight genes to a T7 promoter and a terminator to construct gene expression cassettes T7 tdiAS, T7 tdiBS, T7 tdiCS, T7 tdiDS, T7 tdiES, T7 sfpS, T7 ScCKS, and T7 AtIPKS;

step S2: sequentially linking and ligating six gene expression cassettes obtained in step S1, namely, the T7 tdiAS, the T7 tdiBS, the T7 tdiCS, the T7 tdiDS, the T7 tdiES, and the T7 sfpS, to an *Escherichia coli* expression vector to obtain a recombinant plasmid pC02 comprising six gene expression cassettes tdiAS, tdiBS, tdiCS, tdiDS, tdiES, and sfpS;

step S3: sequentially linking and ligating two gene expression cassettes obtained in step S1, namely, the T7 ScCKS and the T7 AtIPKS, to an *Escherichia coli* expression vector to obtain a recombinant plasmid pU03 comprising two gene expression cassettes ScCKS and AtIPKS; and step S4: simultaneously transforming the recombinant plasmid pC02 obtained in step S2 and the recombinant plasmid pU03 obtained in step S3 into *Escherichia coli* to obtain the recombinant *Escherichia coli* strain capable of producing the terrequinone A.

8. The recombinant *Escherichia coli* strain capable of producing terrequinone A of claim 7, wherein in the step S2, the six gene expression cassettes, namely, the T7 tdiAS, the T7 tdiBS, the T7 tdiCS, the T7 tdiDS, the T7 tdiES, and the T7 sfpS, are sequentially linked and ligated to an EcoRI endonuclease site at a 5'-end of the T7 tdiAS and a HindIII endonuclease site at a 3'-end of the T7 sfpS to obtain EcoRI-T7 tdiAS-T7 tdiBS-T7 tdiCS-T7 tdiDS-T7 tdiES-T7 sfpS-HindIII.

9. The recombinant *Escherichia coli* strain capable of producing terrequinone A of claim 7, wherein in the step S3, the two gene expression cassettes, namely, the T7 ScCKS and the T7 AtIPKS, are sequentially linked and ligated to an EcoRI endonuclease site at a 5'-end of the T7 ScCKS and a HindIII endonuclease site at a 3'-end of the T7 AtIPKS to obtain EcoRI-T7 ScCKS-T7 AtIPKS-HindIII.

* * * * *

SEQUENCE LISTING

```
Sequence total quantity: 42
SEQ ID NO: 1            moltype = DNA  length = 2913
FEATURE                 Location/Qualifiers
source                  1..2913
                        mol_type = other DNA
                        note = Nucleotide sequence of tdiAS gene
                        organism = synthetic construct
SEQUENCE: 1
atggcaccat ctaagactga aattgcacca cttagagcag caaaatatcc atttggtaac  60
attgttgatg ctcttcgtca tgctgctgca cataccgatg agggtatcat cgtctaccat  120
ccaaactcca tctccacctc ctccccacca cagaccgtct cctacaaaga cctgctgcat  180
caggctgagg caaacgcaac tcgtctgttg cagcagaagc tgtgttctcc aaagtccatc  240
gtcctggttc acttcgagtc tgcactggac tccatcgtct ggtactggtc tgtccttctg  300
gctggtggta ttcctgcact gactggtcct ggtatgttct ctcagaaccc tgctgatcgt  360
gaacgtcatc tgcgtcatct gtctgagacc ctgaactctc ctgtctgtct gactcgtcct  420
gcactgttgg caccatttga agagcagact gctgatgacc gtatcaaagc tcgtactgtc  480
gatgagatcc tggctgcacc tgaaatcgct gatgttgctg acgcaccact gcctgcactg  540
actccatctt ctactgacat gcttgcactg atgctgactt ctggttcttc tggtaatgcc  600
aaggctgttc cactgactca tcaacagctg cttgctgcct ttcgtggtaa gtctactgct  660
gcttctctgc gtttcccacg ttctcctttc ctgtcttggg ttcacatgga tcatgttgct  720
aacctggttc attgccacat cttcgctatc gtttctggta tctcccagat ccaagttcct  780
gcacctgacc tgctgatcaa ccctgcacag cttctgaacc tgatctctcg tcaccgtgtc  840
tctcgtacct tcatgccaaa cttcctgtgt gccaagttgc gtcgtcagct ggagtctggt  900
tctccagagt acatccttga ccctggtctg aacctggaaa ccctgtacat cgatactggt  960
ggtgaggcta acgtcactga ggtctgcatt gcactgcaat ctctgctgtc tcgttacggt  1020
gctcctgaca acgtcttcaa gccatccttc ggtatgactg agactgttgc tggttgcatc  1080
ttcaactctc attgtccatc ctatgaccat gcacaacgtc atgagttcgc atgtcttggt  1140
aagcctatgc ctggtgttcg tatgcgtgtc actcgtctgg atactccatc tgaagaggct  1200
gctcctggtg aacgtggttc tctggaagtc actggtgaag ttgtcttcaa gggttactac  1260
aacaaccctg ctgcaactgc tgaggcattc acctctgatg gttggttccg tactggtgat  1320
ctggcattca ttgactccaa tggtaatctg catcttgatg gtcgtactaa ggagatgatc  1380
aacatcaatg gtgtcaaata cctgccatac gaactggatg ctgctcttga gcaggcacag  1440
attcctggtg caactccatc ttacttctgc accttctcct ctcgtgatgc aactatggac  1500
actgaggttg tcgttgtcct gtaccttcca tcctacgtcg agtctgatga tgaagcacgt  1560
ttctctactc aatcctctat catccgtgtt gttgcaatgc atactcgttc tcgtccacgt  1620
gtcgttccac tgcgtccaca ggacatgcca aagtccactc tgggtaagct gtctcgtgca  1680
aagctgaaga ctgcactgga agaaggtcag ttcgcaactc aacaacaaat caacgacgaa  1740
gccatccgtc gttatcagca gaagactcgt gcatctcctg aaactcctga cgaagctgtc  1800
attctggata ttatcaagga acagctggag atccggtctg atgatgacag ctttggcgtc  1860
aacgattcaa tcctgtccat cggtgcaacc tctatggatc tggttgcaat cattcaccgt  1920
atcaacaagt gtcttcagcc atctcagcca ctgcgtctga ctgacatcct gaaagactcc  1980
actgctcgtg gtctggctgt tgcacttgca actggtgctg caccacgttc tcaggatcag  2040
tcttctactc atgtctacga tcctgttgtc actcttcaac cacatggtac taagtctcca  2100
ctgtggctgg ttcatcctgg tgttggtgag gtccttgtct tcgtcaacct tgcacaccac  2160
atcaccgacc gtcctgtcta cgcattccgt gcaaagggtt tcaatgctgc tgctggtctg  2220
cctgagactc cattcacctc tcttgaggag ttgttcacta cctaccgtga tgcaatcaag  2280
gaacgtcaac cacatggtcc atacgcaatc gctggttact ccttcggtgg tatggttgca  2340
ttcgaagtct ccaagctgct tgaacaggat ggtgatgagg ttcgttactg tggttcttgg  2400
aaccttccac cacacatcaa gttccgtatg cgtgaactcg tctgggagga atgcgttatc  2460
catctattct acttcgttgg tctgatgact gaactggctg catacactca caaaccaact  2520
cttcaggagt tcaaccgtgc aaaccgtcgt ctggatgcta tccgttacct gcgtcaacac  2580
tgtgatgctg cacgttggga tgaacttggt ctgtctgagg agtactatct gctgtgggtt  2640
```

```
ggtctggcat ctaacatgca atcccttgct gttgactacg aaccatctgg ttccgtcaag  2700
tgcatggatg tctttgttgc tgatccattg tctcatgttg caaaggaccg tatcgactgg  2760
gttgagggtc gtttgtctgc atggaaggag ttcgttcgtg aggatgtccg tttccatgat  2820
gtccaaggtg cacactacac catgctgaac cgtgagtacg tcgaggcatt cgctggtact  2880
ctgaagaacg tcctgcgtga gcgtggtctg taa                              2913

SEQ ID NO: 2           moltype = DNA  length = 1260
FEATURE                Location/Qualifiers
source                 1..1260
                       mol_type = other DNA
                       note = Nucleotide sequence of tdiBS gene
                       organism = synthetic construct
SEQUENCE: 2
atggctactg aatactggtc tcgtcatctt cgttctgttc ttgcaccact gttcgctgct  60
gctggtactt actctcctga agatcaggag tctcatctgg ccttcattga cgagcacatt  120
gcaccaaacc tgggtccact gccttgggaa ccacatggtc catactctac tccatcttct  180
cttgttggtt ctccattcga tccatctatc aacatcgtct cttctggtaa ggccaaggtt  240
cgtttcgact tcgatgtcat ctctccacct gatcgtactg gtcctgaccc attcgctgag  300
ggatctgctc gtgagatcct tcatcgtctt gctgaccttg ttggtgctga cactcagtgg  360
atgggttatc tgatggatgc tctgtacctg actcctgctg aggctgaggt tgccaaaacc  420
aagctgccac caggtgttgc cattccacca tcttctgttg gtttcgattt cgatggtcct  480
gaacgtactc tgaagttcta catcccatct gttcgtaagg cattggcaac tggtcaggat  540
gtctctgaac tcatgctgaa gactctgcgt ggtttgcagc cacttggttc tgaactcgtt  600
cctgctatgg atctgattgc ctcttacctg tccactcgta ccaacgacgc tatgcttcca  660
cttgttggta tcgactgtct tgatccacgt actcacaaga acgctcgtgt caaatgctac  720
ctgcacacct cttccaactc tttcgctgtt gttcgtgatg tcctgactct tggtggtcgt  780
ctgtctgatg atacctctct gaagcgtgtt gagactctga aatccgtttg gccactgctg  840
atcaacgaac tcgaaggtcc acagtctgat gctgctacta tggatgagtc ctggtccaag  900
cctgaacgtc tgaaccgtac tggttactct ggtatccagt acaccatcga gatcactcct  960
ggtcaggcaa tccctgatac caagatttac gttccattgt tccagtacac cgactcttct  1020
gaggttgctg agcgtaactt cgagtctgca ctgaagaagc tgggtaacga atggggtctg  1080
tctggtaagt accgttctgt tatgcaggaa atcttcaagg atgtcgagaa ctacggtcag  1140
acctacgcat ccttctccta caccgagggt aagggtgtct acaccacctc ctacgtcgct  1200
atgccaatca aggatgaggg tggtggttcc ctggctggtg acttcggttt ccgtaactaa  1260

SEQ ID NO: 3           moltype = DNA  length = 1068
FEATURE                Location/Qualifiers
source                 1..1068
                       mol_type = other DNA
                       note = Nucleotide sequence of tdiCS gene
                       organism = synthetic construct
SEQUENCE: 3
atgcacgcag ctcttgttcc aacttggtct tctccatgtc caatctatac tgaaattcca  60
gatcctggtc caccaccacc agaacagctg caactgaaag tcttggctgt tggtatccca  120
cgtgttgttc gtcttcgtgc tcgtggtatc catcctactg ccaagtctgc ctctcttcca  180
tacgatccat ccattgatgg tgttggtatc gacgaacaaa ccggtatcat gtactacatc  240
cttccactct ctgcctcttg tctggctgag aaagtcaacg ttgaccgtga caaccttgtt  300
ccacttcagc ctggtgcacc aaaaccacaa ccacgtaacg gtcctgagaa cggttacggt  360
atcgcacttg gtgacgctgc tgatcatcgt gctgagactc tggacccaat cgcaattgct  420
ggtctggtca atcctgtctc ctcttcttgg atggcattgc gtactcgtgt tgatggtgag  480
atcactggta agactgttct ggttcttggt gctacttcca agtctggtcg tgctgctgtt  540
ctcgttgcac gtttcctggg tgccaacaaa gtcatcggtg ttgcacgtcg tgaggaaggt  600
ctgcgttctg tcgaaggtct ggatggttgg gtcacttctg gtgacatgct tcctggtgag  660
actggtgttc gtttcgcact tcctgactgg gttggtcctg tccacatcgt cctggactac  720
gttggtggtt ctgttgctgc tggtgttctt ggttctgctg agatcgagga gggtcgtgag  780
ttgcaatacg tccaggttgg taatctggca cttgagcttg gtactggtga gaagcacatg  840
ttcgagacct tgcctggtca tctgatctct cgtaagccaa tctgcattcg tggttctggt  900
atgggttctt tctctcgtcg tgatctggtt cgtgagatgc ctggtttggt tgcattcctt  960
gctcgtatga aggcaccatt cggtatcgca tctgctccaa tgtgtgaggt tgcatccgtc  1020
tggcaggacg aggacaccaa gggttcccgt gtcgtcatcg tcccttaa              1068

SEQ ID NO: 4           moltype = DNA  length = 1311
FEATURE                Location/Qualifiers
source                 1..1311
                       mol_type = other DNA
                       note = Nucleotide sequence of tdiDS gene
                       organism = synthetic construct
SEQUENCE: 4
atgggttcta ttggtgctaa caatgctgtt gctgatccaa ctccactttt ctcttccaga  60
gttcagaaat gggaacctgg tgcaatccgt tctcttcttc cactggaagc ccttcctggt  120
atgatctccc tggttgctgg taagccatct cctgagacct tcccaatcgc tgagatcgct  180
atctctctga aggacactcc tgctggtact ggtcgtatcg ttgttgatgg tgatgaactg  240
aaccaggctc tgcaatacgg tcttcctcgt ggtaacgcac agctcatcca gtggttcgag  300
tctcttcagc gttctgttca tggtctggac gagaatggtg gttggtcttg ttgcatcggt  360
aacggttctc aggagctgat ccatcgtgtc atccaggtct tcactgaccc tggtgatcca  420
gttctgctgg aaactcctgc ataccctggt gttgctggtt tccttcgtgc tgatggtcag  480
gagctgatcc ctgtctactc tgacgctcag ggtctgaatc ctgcctctct ggaacaggca  540
ctgtctgaat ggcctggtga ctctccacgt cctaaggtcc tgtacaccac tccaactggt  600
tccaacccaa ccggtcaatc ttgcactgag tctcgtaagg ctgagatcct gcgtcttgcc  660
```

```
aagcgtttca acttcatcat cctggaagac gatgcctact actacctgaa ctacggtgac  720
gacaaacagc gtgcacgttc ctaccttgct ctggaacgtg acgtcaacgg tgagtctggt  780
cgtgtcgttc gtttcgattc tctgtccaag atcgtctctc ctggtatgcg tcttggtatc  840
ctgactgcac aagctgctgt tgttgacaag gttgttcgta tcactgagaa catcaacctt  900
caaccatcct ccaccaccca actgcttgct ctgtcccttc ttcgtcactg ggtcaagct   960
ggtttcctga agcactgtgc tgaagctgct gaggtctacc gtcgtcgtcg tgacgtcttc  1020
gtctctgctg ctgagcgtca ccttcagggt cgtgctactt gggtcgttcc aactgctggt  1080
atgttcgtct ggctggaact caagttgcca cctgagatgg actccttcga gcttctgaag  1140
tcccagggta tgaagaacgg tgttctcgct atccctggtg ttgccttcat gcctggtaac  1200
gaacagacct gctacatccg tgtctccttc tctctcgttc ctgagcgtga tatggatgag  1260
gcatgtcgtc gtatcgctgg tctggtcgat cgttgcgcct gccactccta a           1311

SEQ ID NO: 5            moltype = DNA  length = 953
FEATURE                 Location/Qualifiers
source                  1..953
                        mol_type = other DNA
                        note = Nucleotide sequence of tdiES gene
                        organism = synthetic construct
SEQUENCE: 5
atggttaaca gaccatacgc aaatatgaat gatcttgcta atgctgttgc tgaatctgtt  60
cagaaatatc tggacaactc tggtcaagcc agaaacggtc tgttccagaa aaccaacaac  120
ggtgaacgtg acatcgaaac cgagcgtctg gcactccagc accagctctt ccacctgact  180
ctggacggta aactccagtt gtctccactg ccttctccag ttcaatccgt tctggacatc  240
gccactggtg actccacctg ggtccatgcc ttcgctgaac agaacccatc tgcctacatc  300
gttgccaacg acccatctcc aacctccaag atcccacttg gtctgtctgt catcccagac  360
gcttccgatg ccaacgaacc ttggacctac accagacagt tcgacttcgt ccactgtaga  420
cagcaccatc gtcgtcttga cgaaccacgt ctgttcaagc aggcattctc tttctgactc  480
ctggtggttg gctggagatg caggaactct ccaaccctgt cacctctgat gacggtactc  540
tgtccgagaa caacccactg tctcagtggg gtcgtcttct gatcgaggca tccaagaaga  600
tgaaccgtcc tgtcgataac cctgccaaat acgagacctg gatgcgtgag gctggtttcg  660
tcaactgcca caccgttgcc tacaactggc ctaccaaccc ttggcctgct gacgagaagg  720
gtaagacctt gggtttgtgg aacctgtaca acgtcttgca gcgtttcgaa gagttctctg  780
tcgccttgtt ggtcaaagtc ctcggttggg agatggacga tgctaagacc ttcttgggta  840
acgtcaagga ggagctgatg aacgagggtg ttcatggtta ctggcctgtc tacgttgtct  900
acggtcagaa gccagctgca cctggttccg acgtcatcac cgactccgag taa         953

SEQ ID NO: 6            moltype = DNA  length = 498
FEATURE                 Location/Qualifiers
source                  1..498
                        mol_type = other DNA
                        note = Nucleotide sequence of sfpS gene
                        organism = synthetic construct
SEQUENCE: 6
atgaaaatct acggtatcta catggatcgt ccactctcac aggaggagaa cgaacgtttc  60
atgtcattca tctcacctga gaagcgtgag aagtgtcgtc gtttctatca caaggaagat  120
gcacatcgta ctctgctggg tgacgtcctg gttcgttctg tgatctcacg tcagtaccag  180
ttggacaagt ctgacatccg tttctcaact caggagtatg gtaagccatg cattcctgac  240
ctgcctgatg cacacttcaa catctctcac tctggacgtt gggtgatctg tgcattcgac  300
tcacagccaa tcggaatcga catcgagaag accaagccaa tctcacttga gatgcctaag  360
cgtttcttct ccaagactga gtactctgac ctgcttgcca aggacaagga cgagcagacc  420
gactacttct accatctctg gtccatgaag gaatccttca tcaagcaagg acgtcaacgt  480
ctcatcgcat ctgcataa                                                498

SEQ ID NO: 7            moltype = DNA  length = 1749
FEATURE                 Location/Qualifiers
source                  1..1749
                        mol_type = other DNA
                        note = Nucleotide sequence of ScCKS gene
                        organism = synthetic construct
SEQUENCE: 7
atggttcaag agtcacgtcc tggttctgtt cgttcatact ctgttggcta ccaagcacgt  60
tcacgttcat catcacaacg tcgtcactcc ttgactcgtc agcgttcctc acaacgtctg  120
attcgtacca tctccatcga gtctgatgtg tccaacatca ctgacgatga cgacttgcgt  180
gctgtgaatg agggtgttgc tggtgtgcaa ctggacgtct ctgagactgc caacaagggt  240
ccacgtcgtg catctgccac tgatgtcact gattccttgg gttcaacttc atctgagtac  300
atcgagattc cattcgtgaa ggagaccttg gatgcatcct tgccatccga ctacctgaag  360
caggacatct tgaatctgat tcagtccctg aaaatctcca agtggtacaa caacaagaag  420
atccaacctg tggcacaaga catgaacctg gtcaaaatct ctggtgcaat gaccaacgca  480
atcttcaagg ttgagtaccc taagctgcca tccttgctgt tgcgtatcta cggtcctaac  540
atcgacaaca tcattgaccg tgagtatgag ttgcagatcc tggcacgtct gtccttgaag  600
aacatcggtc catcactgta tggctgcttc gtcaacggtc gtttcgagca gttcctggag  660
aactccaaga ccttgaccaa ggacgacatc cgtaactgga agaactctca acgtatcgca  720
cgtcgtatga aggagttgca tgttggtgtt ccactgttgt catctgaacg taagaacggt  780
tctgcctgtt ggcagaagat caaccagtgg ttgcgtacca tcgagaaggt tgaccagtgg  840
gttggtgatc ctaagaacat tgagaactcc ttgttgtgtg agaactggtc caagttcatg  900
gacattgtgg atcgttacca caagtggctg atctcccaag aacagggtat cgagcaagtg  960
aacaagaatc tgatcttctg ccacaatgat gcacagtatg gcaacttgct gttcactgca  1020
cctgtcatga acactccatc actgtacact gcaccatcct ccacctcact gacctcacag  1080
tcatcatcct tgttcccatc atcatccaac gtgattgttg atgacatcat caacccacct  1140
```

-continued

```
aagcaggagc aatcacaaga ctccaagttg gtggtgatcg acttcgagta tgctggtgcc  1200
aaccctgctg cctatgacct tgccaatcac ctgtctgagt ggatgtatga ctacaacaac  1260
gccaaggcac cacatcagtg ccacgctgat cgttaccctg acaaggaaca ggtcttgaac  1320
ttcttgtact cctatgtctc acatcttcgt ggtggtgcta aggaacctat cgatgaagag  1380
gttcaacgtc tgtacaagtc catcattcag tggcgtccaa ctgttcaact cttctggtca  1440
ctgtgggcaa tccttcagtc tggcaagttg gagaagaagg aagcatccac tgcaatcact  1500
cgtgaagaga tcggtcctaa cggcaagaag tacatcatca agactgaacc tgagtcacct  1560
gaagaagact tcgttgagaa cgacgatgaa cctgaagctg gtgtctccat cgacaccttc  1620
gactacatgg catacggtcg tgacaagatc gctgtcttct ggggtgatct gattggcctt  1680
ggcatcatca ctgaagaaga gtgcaagaac ttctcctcct tcaagttcct cgacacttcc  1740
tacttgtaa                                                          1749

SEQ ID NO: 8           moltype = DNA  length = 919
FEATURE                Location/Qualifiers
source                 1..919
                       mol_type = other DNA
                       note = Nucleotide sequence of AtIPKS gene
                       organism = synthetic construct
SEQUENCE: 8
gaacgagctg gagaagattc acgatgagaa tctggaggtt gttgcctgtc agcttcgtca  60
agctatgctg gagggttctg caccttccaa ggtcatcggt atggactggt ccaagcgtcc  120
tggttcatct gaaatctctt gtgatgtgga tgacatcggt gatcagaagt cctctgagtt  180
ctccaagttc gttgttgtcc acggtgctgg ttccttcggt cacttccagg catcacgttc  240
tggtgttcac aagggtggtc ttgagaagcc tatcgtgaag gctggcttcg ttgctactcg  300
tatctctgtc accaacctga accttgagat cgttcgtgca cttgcacgtg agggtatccc  360
taccatcggt atgtctccat tctcatgtgg ttggtcaacc tccaagcgtg atgttgcatc  420
tgctgatctt gccactgttg ccaagaccat cgactctggc ttcgttcctg ttctgcatgg  480
tgatgctgtc ctggacaaca tccttggctg caccatcttg tctggtgatg tgatcatccg  540
tcatcttgct gatcacttga agcctgagta tgttgtgttc ctgactgatg tccttggtgt  600
gtacgatcgt ccaccatcac catctgaacc agatgctgtg ctgctgaagg agatcgctgt  660
tggtgaagat ggttcatgga aggttgtcaa cccactgttg gagcacactg acaagaaggt  720
tgactactct gttgcagcac acgacactac tggtggtatg gagaccaaaa tctctgaagc  780
tgccatgatt gctaagctgg gtgtggatgt gtacatcgtc aaggctgcca ccactcactc  840
acagcgtgca ctgaacggtg acttgcgtga ctctgttcct gaagactggc ttggtactat  900
catccgtttc tccaagtaa                                               919

SEQ ID NO: 9           moltype = DNA  length = 19
FEATURE                Location/Qualifiers
source                 1..19
                       mol_type = other DNA
                       note = T7 promoter sequence
                       organism = synthetic construct
SEQUENCE: 9
taatacgact cactatagg                                               19

SEQ ID NO: 10          moltype = DNA  length = 47
FEATURE                Location/Qualifiers
source                 1..47
                       mol_type = other DNA
                       note = T7 terminator sequence
                       organism = synthetic construct
SEQUENCE: 10
tagcataacc ccttggggcc tctaaacggg tcttgagggg ttttttg                47

SEQ ID NO: 11          moltype = DNA  length = 40
FEATURE                Location/Qualifiers
source                 1..40
                       mol_type = other DNA
                       note = P1 of T7 tdiAS
                       organism = synthetic construct
SEQUENCE: 11
gaatcctaat acgactcact ataggatggc accatctaag                        40

SEQ ID NO: 12          moltype = DNA  length = 47
FEATURE                Location/Qualifiers
source                 1..47
                       mol_type = other DNA
                       note = P2 of T7 tdiAS
                       organism = synthetic construct
SEQUENCE: 12
gtattcagta gccatcctat agtgagtcgt attacaaaaa acccctc                47

SEQ ID NO: 13          moltype = DNA  length = 49
FEATURE                Location/Qualifiers
source                 1..49
                       mol_type = other DNA
                       note = P3 of T7 tdiBS
                       organism = synthetic construct
SEQUENCE: 13
```

-continued

```
ttgaggggtt ttttgtaata cgactcacta taggatggct actgaatac            49

SEQ ID NO: 14          moltype = DNA  length = 47
FEATURE                Location/Qualifiers
source                 1..47
                       mol_type = other DNA
                       note = P4 of T7 tdiBS
                       organism = synthetic construct
SEQUENCE: 14
aagagctgcg tgcatcctat agtgagtcgt attacaaaaa acccctc              47

SEQ ID NO: 15          moltype = DNA  length = 49
FEATURE                Location/Qualifiers
source                 1..49
                       mol_type = other DNA
                       note = P5 of T7 tdiCS
                       organism = synthetic construct
SEQUENCE: 15
ttgaggggtt ttttgtaata cgactcacta taggatgcac gcagctctt            49

SEQ ID NO: 16          moltype = DNA  length = 47
FEATURE                Location/Qualifiers
source                 1..47
                       mol_type = other DNA
                       note = P6 of T7 tdiCS
                       organism = synthetic construct
SEQUENCE: 16
accaatagaa cccatcctat agtgagtcgt attacaaaaa acccctc              47

SEQ ID NO: 17          moltype = DNA  length = 49
FEATURE                Location/Qualifiers
source                 1..49
                       mol_type = other DNA
                       note = P7 of T7 tdiDS
                       organism = synthetic construct
SEQUENCE: 17
ttgaggggtt ttttgtaata cgactcacta taggatgggt tctattggt            49

SEQ ID NO: 18          moltype = DNA  length = 48
FEATURE                Location/Qualifiers
source                 1..48
                       mol_type = other DNA
                       note = P8 of T7 tdiDS
                       organism = synthetic construct
SEQUENCE: 18
atggtctgtt aaccatccta tagtgagtcg tattacaaaa aacccctc             48

SEQ ID NO: 19          moltype = DNA  length = 50
FEATURE                Location/Qualifiers
source                 1..50
                       mol_type = other DNA
                       note = P9 of T7 tdiES
                       organism = synthetic construct
SEQUENCE: 19
ttgaggggtt ttttgtaata cgactcacta taggatggtt aacagaccat           50

SEQ ID NO: 20          moltype = DNA  length = 47
FEATURE                Location/Qualifiers
source                 1..47
                       mol_type = other DNA
                       note = P10 of T7 tdiES
                       organism = synthetic construct
SEQUENCE: 20
accgtagatt ttcatcctat agtgagtcgt attacaaaaa acccctc              47

SEQ ID NO: 21          moltype = DNA  length = 49
FEATURE                Location/Qualifiers
source                 1..49
                       mol_type = other DNA
                       note = P11 of T7 spfS
                       organism = synthetic construct
SEQUENCE: 21
ttgaggggtt ttttgtaata cgactcacta taggatgaaa atctacggt            49

SEQ ID NO: 22          moltype = DNA  length = 35
FEATURE                Location/Qualifiers
source                 1..35
                       mol_type = other DNA
                       note = P12 of T7 spfS
```

```
                        organism = synthetic construct
SEQUENCE: 22
aagcttcaaa aaacccctca agacccgttt agagg                          35

SEQ ID NO: 23           moltype = DNA  length = 38
FEATURE                 Location/Qualifiers
source                  1..38
                        mol_type = other DNA
                        note = P13 of T7 ScCKS
                        organism = synthetic construct
SEQUENCE: 23
gaatcctaat acgactcact ataggatggt tcaagagt                       38

SEQ ID NO: 24           moltype = DNA  length = 48
FEATURE                 Location/Qualifiers
source                  1..48
                        mol_type = other DNA
                        note = P14 of T7 ScCKS
                        organism = synthetic construct
SEQUENCE: 24
cttctccagc tcgttcccta tagtgagtcg tattacaaaa aacccctc            48

SEQ ID NO: 25           moltype = DNA  length = 50
FEATURE                 Location/Qualifiers
source                  1..50
                        mol_type = other DNA
                        note = P15 of T7 AtIPKS
                        organism = synthetic construct
SEQUENCE: 25
ttgaggggtt ttttgtaata cgactcacta tagggaacga gctggagaag          50

SEQ ID NO: 26           moltype = DNA  length = 35
FEATURE                 Location/Qualifiers
source                  1..35
                        mol_type = other DNA
                        note = P16 of T7 AtIPKS
                        organism = synthetic construct
SEQUENCE: 26
aagcttcaaa aaacccctca agacccgttt agagg                          35

SEQ ID NO: 27           moltype = DNA  length = 21
FEATURE                 Location/Qualifiers
source                  1..21
                        mol_type = other DNA
                        note = Primer tdiA-F
                        organism = synthetic construct
SEQUENCE: 27
tccgtcaagt gcatggatgt c                                         21

SEQ ID NO: 28           moltype = DNA  length = 21
FEATURE                 Location/Qualifiers
source                  1..21
                        mol_type = other DNA
                        note = Primer tdiA-R
                        organism = synthetic construct
SEQUENCE: 28
cagaccacgc tcacgcagga c                                         21

SEQ ID NO: 29           moltype = DNA  length = 21
FEATURE                 Location/Qualifiers
source                  1..21
                        mol_type = other DNA
                        note = Primer tdiB-F
                        organism = synthetic construct
SEQUENCE: 29
gcactgaaga agctgggtaa c                                         21

SEQ ID NO: 30           moltype = DNA  length = 21
FEATURE                 Location/Qualifiers
source                  1..21
                        mol_type = other DNA
                        note = Primer tdiB-R
                        organism = synthetic construct
SEQUENCE: 30
acggaaaccg aagtcaccag c                                         21

SEQ ID NO: 31           moltype = DNA  length = 21
FEATURE                 Location/Qualifiers
source                  1..21
```

```
                          mol_type = other DNA
                          note = Primer tdiC-F
                          organism = synthetic construct
SEQUENCE: 31
atctctcgta agccaatctg c                                      21

SEQ ID NO: 32             moltype = DNA  length = 21
FEATURE                   Location/Qualifiers
source                    1..21
                          mol_type = other DNA
                          note = Primer tdiC-R
                          organism = synthetic construct
SEQUENCE: 32
gacgatgacg acacgggaac c                                      21

SEQ ID NO: 33             moltype = DNA  length = 21
FEATURE                   Location/Qualifiers
source                    1..21
                          mol_type = other DNA
                          note = Primer tdiD-F
                          organism = synthetic construct
SEQUENCE: 33
atgttcgtct ggctggaact c                                      21

SEQ ID NO: 34             moltype = DNA  length = 21
FEATURE                   Location/Qualifiers
source                    1..21
                          mol_type = other DNA
                          note = Primer tdiD-R
                          organism = synthetic construct
SEQUENCE: 34
gcaacgatcg accagaccag c                                      21

SEQ ID NO: 35             moltype = DNA  length = 21
FEATURE                   Location/Qualifiers
source                    1..21
                          mol_type = other DNA
                          note = Primer tdiE-F
                          organism = synthetic construct
SEQUENCE: 35
aagaccttgg gtttgtggaa c                                      21

SEQ ID NO: 36             moltype = DNA  length = 21
FEATURE                   Location/Qualifiers
source                    1..21
                          mol_type = other DNA
                          note = Primer tdiE-R
                          organism = synthetic construct
SEQUENCE: 36
gacgtcggaa ccaggtgcag c                                      21

SEQ ID NO: 37             moltype = DNA  length = 21
FEATURE                   Location/Qualifiers
source                    1..21
                          mol_type = other DNA
                          note = Primer sfp-F
                          organism = synthetic construct
SEQUENCE: 37
tctcactctg gacgttgggt g                                      21

SEQ ID NO: 38             moltype = DNA  length = 21
FEATURE                   Location/Qualifiers
source                    1..21
                          mol_type = other DNA
                          note = Primer sfp-R
                          organism = synthetic construct
SEQUENCE: 38
tgcagatgcg atgagacgtt g                                      21

SEQ ID NO: 39             moltype = DNA  length = 21
FEATURE                   Location/Qualifiers
source                    1..21
                          mol_type = other DNA
                          note = Primer ScCK-F
                          organism = synthetic construct
SEQUENCE: 39
ggtcctaacg gcaagaagta c                                      21

SEQ ID NO: 40             moltype = DNA  length = 21
```

-continued

```
FEATURE                 Location/Qualifiers
source                  1..21
                        mol_type = other DNA
                        note = Primer ScCK-R
                        organism = synthetic construct
SEQUENCE: 40
ggaggagaag ttcttgcact c                                          21

SEQ ID NO: 41           moltype = DNA  length = 21
FEATURE                 Location/Qualifiers
source                  1..21
                        mol_type = other DNA
                        note = Primer AtIPK-F
                        organism = synthetic construct
SEQUENCE: 41
ccactgttgg agcacactga c                                          21

SEQ ID NO: 42           moltype = DNA  length = 21
FEATURE                 Location/Qualifiers
source                  1..21
                        mol_type = other DNA
                        note = Primer AtIPK-R
                        organism = synthetic construct
SEQUENCE: 42
ggagaaacgg atgatagtac c                                          21
```